(12) United States Patent
Hubbard et al.

(10) Patent No.: US 7,795,583 B1
(45) Date of Patent: Sep. 14, 2010

(54) LONG RANGE ACTIVE THERMAL IMAGING SYSTEM AND METHOD

(75) Inventors: Richard F Hubbard, Burke, VA (US); Arne W Fliflet, Alexandria, VA (US); Jeffrey H Bowles, Burke, VA (US); David A Kidwell, Alexandria, VA (US); Melissa K. Hornstein, Washington, DC (US); Geoffrey B. Smith, Manassas, VA (US); David Lewis, III, Mountain View, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/539,380

(22) Filed: Oct. 6, 2006

Related U.S. Application Data

(60) Provisional application No. 60/726,757, filed on Oct. 7, 2005.

(51) Int. Cl.
*G01J 5/00* (2006.01)
(52) U.S. Cl. .................................................. 250/338.1
(58) Field of Classification Search ................. 250/330, 250/338.1
See application file for complete search history.

(56) References Cited

U.S. PATENT DOCUMENTS

| | | | |
|---|---|---|---|
| 5,592,170 A * | 1/1997 | Price et al. | 342/22 |
| 6,169,277 B1 * | 1/2001 | Feher et al. | 219/702 |
| 6,343,534 B1 | 2/2002 | Khanna et al. | |
| 6,501,414 B2 * | 12/2002 | Arndt et al. | 342/22 |
| 6,746,510 B2 | 6/2004 | Kurihara et al. | |
| 6,771,798 B1 | 8/2004 | Haas et al. | |
| 6,802,907 B2 | 10/2004 | Lewis, III et al. | |
| 6,982,666 B2 * | 1/2006 | Temes et al. | 342/22 |
| 7,022,198 B2 | 4/2006 | Bruce et al. | |
| 7,173,560 B2 * | 2/2007 | Li et al. | 342/22 |

(Continued)

OTHER PUBLICATIONS

L. C. Aaomodt, J. W. Maclachan Spicer, and J. C. Murphy, "Analysis of Characteristic Thermal Transit Times for Time-Resolved Infrared Radiometry Studies of Multilayered Coatings", J. Appl. Phys. 68, 6087-98 (1990).

(Continued)

*Primary Examiner*—David P Porta
*Assistant Examiner*—Marcus H Taningco
(74) *Attorney, Agent, or Firm*—Amy L. Ressing; L. George Legg

(57) ABSTRACT

A long-range active thermal imaging system includes an electromagnetic radiation source in the range of from about 10 GHz to about 500 GHz; a beam controller for receiving and retransmitting the electromagnetic radiation in a desired direction toward and onto a surface of a target, thereby heating the target and producing an infrared radiation emission from the target surface; and an infrared imager, e.g. an infrared camera coupled to a processor and display, for receiving the target's infrared radiation emission and generating a thermal image of the target. The radiation source may be selected such that the radiation penetrates into the target to provide a thermal signature, e.g. from subsurface features or objects. The thermal signature exhibits rapid changes that can be monitored in real time. This may allow surface or subsurface details or objects to be detected that would not otherwise be apparent.

21 Claims, 8 Drawing Sheets

U.S. PATENT DOCUMENTS

| | | | |
|---|---|---|---|
| 2003/0010919 A1* | 1/2003 | DiMarzio et al. | 250/347 |
| 2004/0007122 A1* | 1/2004 | Seregelyi et al. | 89/1.13 |
| 2004/0081221 A1 | 4/2004 | Sandvoss | |

OTHER PUBLICATIONS

S. A. Telenkov, G. Vargas, J. S. Nelson, and T. E. Milner, "Coherent Thermal Wave Imaging of Subsurface Chromophores in Biological Materials," Phys. Med. Biol. 47, 657-71 (2002).

R. Osiander, J. W. M. Spicer, and J. C. Murphy, "Thermal Imaging of Subsurface Microwave Absorbers in Dielectric Materials," Thermosense XVI, SPIE vol. 2245, SPIE—the International Society for Optical Engineering, pp. 111-119 Bellingham, WA, 1994.

J. R. Simard, "Improved Landmine Detection Capability (ILDC): Systematic Approach to the Detection of Buried Mines using Passive IR Imaging," in Detection and Remediation Technologies for Mines and Minelike Targets, SPIE vol. 2765, p. 489-500, SPIE—the International Society for Optical Engineering, Bellingham, WA, 1996.

W. Fliflet, R. W Bruce,. R. P Fischer, D .Lewis, III; L. K Kurihara,. B.A Bender, G.-M Chow,.and R. J Rayne, "A Study of Millimeter-Wave Sintering of Fine-Grained Alumina Compacts," IEEE Trans. Plasma Sci. 28, pp. 924-935 (2000).

T. Sakagami, S. Kuba, T. Komiyama, and H. Suzuki, "Proposal of a New Thermographical Nondestructive Testing Technique Using Microwave Heating," in Thermosense XXI, SPIE vol. 3700, SPIE—the International Society for Optical Engineering, pp. 99-103, Bellingham, WA, 1999.

Charles A. DiMarzio, Carey M. Rappaport, Wen Li, Gerhard O. Sauermann, Herman E. Scott, "Microwave-enhanced Infrared Thermography," in Detection and Remediation Technologies for Mines and Minelike Targets IV, SPIE vol. 3392, SPIE—the International Society for Optical Engineering, pp. 1103-1110, Bellingham, WA, 1998.

L. J. Carter, M. J. O'Sullivan, Y. J. Hung, and J. C.-C. Teng, "Thermal Imaging for Landmine Detection," in Detection of Abandoned Landmines, IEE Conference Publication No. 458, pp. 110-114, IEE, 1998.

S. I. Bragin,; I. V. Bragin, V. P. Sgibnev, S. E. Chadov, V. I. Gusevsky, Y. B. Bragina, A. A. Morozov, V. V. Tsutskov, and A. F. Zerrouk, "Remote Detection of Objects in Soil Using a Microwave and IR Scanner," in 2nd International Conference on Microwave and Millimeter Wave Technology, 2000, (ICMMT 2000), Institute of Electrical and Electronics Engineers (IEEE), p. 607-10, Piscataway, NJ, 2000.

Taner R. Oktar, Carey M. Rappaport, and Charles A. DiMarzio, "Effects of Surface Roughness on Microwave Heating of Soil for Detection of Buried Land Mines", Detection and Remediation Technologies for Mines and Minelike Targets V, Proc., SPIE vol. 4038, SPIE—the International Society for Optical Engineering, pp. 200-208, Bellingham, WA, 2000.

P. J. Riu, K. R. Foster, D. W. Blick, and E. R. Adair, "A Thermal Model for Human Thresholds of Microwave-Evoked Warmth Sensations", Bioelectromagnetics, vol. 18, pp. 578-583 (1996).

Gerald C. Holst, Common Sense Approach to Thermal Imaging, pp. 151-155, 265, 268-275, SPIE—the International Society for Optical Engineering, Bellingham, WA, 2001.

Granatstein et al., High-power Microwave Sources and Technoloogies, Ch. 6, "Gyrotron Oscillators and Amplifiers", pp. 155-169, IEEE Press Series on RF and Microwave Technology 2001.

Naval Studies Board, An Assessment of Non-Lethal Weapons Science and Technology (2003), pp. 30-31 National Academies Press, Washington, DC, 2003.

D. Lewis, M. A. Imam, L. K. Kurihara, A. W. Fliflet, A. Kinkead, S. Miserendino, S. Egorov, R. W. Bruce, S. Gold, A. M. Jung, "Material processing with a high frequency millimeter-wave source," Materials and Manufacturing Processes, vol. 18,No. 2, pp. 151-167 (2003).

* cited by examiner

LONG RANGE ACTIVE THERMAL IMAGING SYSTEM AND METHOD

CROSS-REFERENCE TO RELATED APPLICATIONS

This Application is a Non-Prov of Prov (35 USC 119(e)) application 60/726,757 filed on Oct. 7, 2005, incorporated herein by reference.

FIELD OF THE INVENTION

The present invention relates to a system and method for active thermal imaging a remote target. More particularly, the invention relates to acquiring an infrared image of a remote target by heating the target with millimeter-length electromagnetic radiation to obtain an enhanced infrared image of the target.

BACKGROUND OF THE INVENTION

Thermal imaging is one of a number of techniques for examining or identifying targets or objects. One such technique is passive thermal imaging.

Passive thermal imaging, in which temperature differences in different portions of a target area are detected using infrared cameras or imaging techniques, for example, as described in Gerald C. Hoist, *Common Sense Approach to Thermal Imaging*, SPIE—the International Society for Optical Engineering, Bellingham, Wash., 2001, has been used for many years. With the use of advanced detectors such as high resolution focal plane arrays and microbolometers, small differences in temperature may be readily detected. However, if the target does not produce its own thermal signature and has remained at the same location for some time, differences in temperature within the target or between the target and background region may be too small to detect.

Passive thermal imaging is routinely used in a variety of situations, including surveillance, nondestructive testing (NDT), electrical/mechanical inspection, building inspection, detection of buried objects, and process/quality control.

Another technique, termed active thermal imaging, involves using an external heating source to enhance thermal contrasts in a target area. These have generally been done over short ranges for nondestructive evaluation applications. Time Resolved Infrared Radiometry (TRIR), an example of such a technique, is described in L. C. Aaomodt, J. W. Maclachan Spicer, and J. C. Murphy, "Analysis of Characteristic Thermal Transit Times for Time-Resolved Infrared Radiometry Studies of Multilayered Coatings", J. Appl. Phys. 68, 6087 (1990). In most cases, a laser or flashlamp is used to heat the region of the target close to the surface. Because the optical radiation does not penetrate into most targets, thermal diffusion plays a major role. Although the heating originates from the surface, the time-dependent temperature profiles can give information about defects or objects beneath the surface. Subsurface features or objects are eventually heated through thermal diffusion, but their temperature can be different from that of surrounding material. The characteristic transit time for thermal diffusion to heat a subsurface feature at a depth d is $t_d = d^2/\alpha_d$, where $\alpha_d$ is the thermal diffusivity, and the time for that signature to diffuse back to the surface is $2t_d$. This process can be used to image or detect the subsurface feature.

There have been also several reports of using conventional microwave sources to provide the heating. Most have involved sources at the commercial S-band frequency of 2.45 GHz. An example is crack detection in concrete structures, for example as described in S. A. Telenkov, G. Vargas, J. S. Nelson, and T. E. Milner, "Coherent Thermal Wave Imaging of Subsurface Chromophores in Biological Materials," Phys. Med. Biol. 47, 657 (2002). Other applications are directed to schemes to detect buried mines and unexploded ordinance using microwave heating, e.g. as described in U.S. Pat. No. 6,343,534, S. M. Khanna et al., issued Feb. 5, 2002. TRIR imaging of subsurface microwave absorbers in dielectrics using an X-band (10 GHz) microwave heating source has also been demonstrated, as described in R. Osiander, J. W. M. Spicer, and J. C. Murphy, "Thermal Imaging of Subsurface Microwave Absorbers in Dielectric Materials," Thermosense XVI, SPIE Vol. 2245, SPIE—the International Society for Optical Engineering, Bellingham, Wash., 1994, p. 111, and in U.S. Pat. No. 6,183,126. J. C. Murphy et al., issued Feb. 6, 2001.

Although it does not use an artificial active source, there is a related passive method that has been used in the past. This method relies on the differential heating (or cooling) that occurs at sunrise or sunset, so that the sun in effect becomes an active heating source. Material that has sufficient thermal inertia compared to its surroundings may maintain its temperature after sunset for some period of time. This method has been used for military targets, including detection of subsurface mines, e.g. as described in J. R. Simard, "Improved Landmine Detection Capability (ILDC): Systematic Approach to the Detection of Buried Mines using Passive IR Imaging," in *Detection and Remediation Technologies for Mines and Minelike Targets, SPIE* Vol. 2765, SPIE—the International Society for Optical Engineering, Bellingham, Wash., 1996, p. 489.

For the current active thermal imaging methods that use conventional long wavelength microwaves as the heating source, extending the range beyond a few meters presents fundamental challenges. For a given range, the heating radiation must provide sufficient intensity to raise the surface temperature in the target area by a detectable amount. Conventional S-band microwave sources operating at 2.45 GHz are not ideal because the radiation cannot be focused with a reasonable antenna size, and radiation at this frequency does not couple well to most materials. Thus, the amount of energy required to produce a detectable thermal signature can become unacceptably large.

The current active thermal imaging methods that use optical sources such as lasers or flashlamps provide surface heating and are well suited for many short range applications in a controlled environment. The use of lasers, e.g. as suggested in U.S. Patent Application No. 20040081221, R. Sandvoss, published Apr. 29, 2004, could be applied for longer range remote sensing applications, but lasers with sufficient intensity to produce a strong thermal signature and power to illuminate a large area generally pose an unacceptable eye safety risk. In addition, the scaling of such systems to high average power is generally less favorable than for microwave or millimeter-wave devices.

BRIEF SUMMARY OF THE INVENTION

The present invention provides a method for heating an area with electromagnetic radiation at a substantial distance from the source of that radiation. Objects or features within the irradiated area are heated at different rates due to differences in electromagnetic absorption and thermal properties. These small temperature differences are detected with an infrared imaging device. This makes it possible to identify objects or examine features that would not otherwise be apparent.

According to the invention, a long-range active thermal imaging system includes an electromagnetic radiation source in the range of from about 10 GHz to about 500 GHz; a beam controller an electromagnetic radiation source for emitting electromagnetic radiation in the range of from about 10 GHz to about 500 GHz; a beam controller for receiving and retransmitting the electromagnetic radiation in a desired direction toward and onto a surface of a target to thereby produce an infrared radiation emission from the target surface; and an infrared imager, e.g. an infrared camera coupled to a processor and display, for receiving the target's infrared radiation emission and generating a thermal image of the target.

Also according to the invention, a method for active microwave IR imaging includes applying the radiation from the system to heat the target and processing the infrared signature obtained from the target to produce a two-dimensional temperature map of the target area. This may allow surface or subsurface details or objects to be detected that would not otherwise be apparent. The infrared signature information data may be further processed by techniques such as hyperspectral imaging to provide very detailed information about a target and its spectral characteristics.

The invention has a number of advantages and features when compared with alternative imaging and remote sensing techniques, as follows.

(1) High power sources of electromagnetic radiation with appropriate parameters are available and offer a relatively mature and robust technology that scales to very high average power. Continuous wave (CW) gyrotron sources of high frequency microwave (millimeter-wave) radiation appear to be particularly well-suited for long range active thermal imaging applications. They can potentially be deployed on a vehicle.

(2) Millimeter-wave radiation can be formed into a beam and projected long distance with a relatively small focusing system or antenna. In comparison, the antenna size required for conventional long wavelength microwave systems with long standoff distances is prohibitive large, and such systems have only been used for very short range applications.

(3) The required energy on target to produce a measurable signature is relatively modest. Longer than millimeter wavelength microwaves penetrate more deeply and generally require substantially more energy on target to produce the same thermal signature.

(4) The return radiation is in the infrared, which has a very mature detection technology and allows imaging to be done at high resolution. Resolution can be a severe limitation for radar systems, even at high frequencies.

(5) If the source is sufficiently powerful, the system has the potential for rapid scanning rates (>10 $m^2$/s) at standoff distances of hundreds of meters. Other active remote sensing concepts are generally far slower.

(6) Both the heating radiation and return signal generally propagate well in the atmosphere. Some alternative imaging schemes, such as those involving terahertz sources, suffer substantially more degradation from absorption and scattering.

(7) The dwell time and radiation intensity on target are potentially adjustable. Thus, larger thermal contrasts can be produced in an area that the user wishes to examine more carefully.

(8) The radiation penetrates into nonmetallic objects, which makes it easier to produce a thermal signature from subsurface features or objects. Optical or laser heating sources for active thermal imaging generally involve only heating of the surface.

(9) The temporal rise and fall of the thermal signature changes very rapidly and can be monitored in real time. This is a common feature of active techniques but is often not useful for passive thermal imaging because the temperature changes are so slow.

(10) With appropriate focusing optics and beam power, the intensity and dwell time on target can be increased to the point where the target is damaged or destroyed.

DETAILED DESCRIPTION OF THE INVENTION

Figure 1:
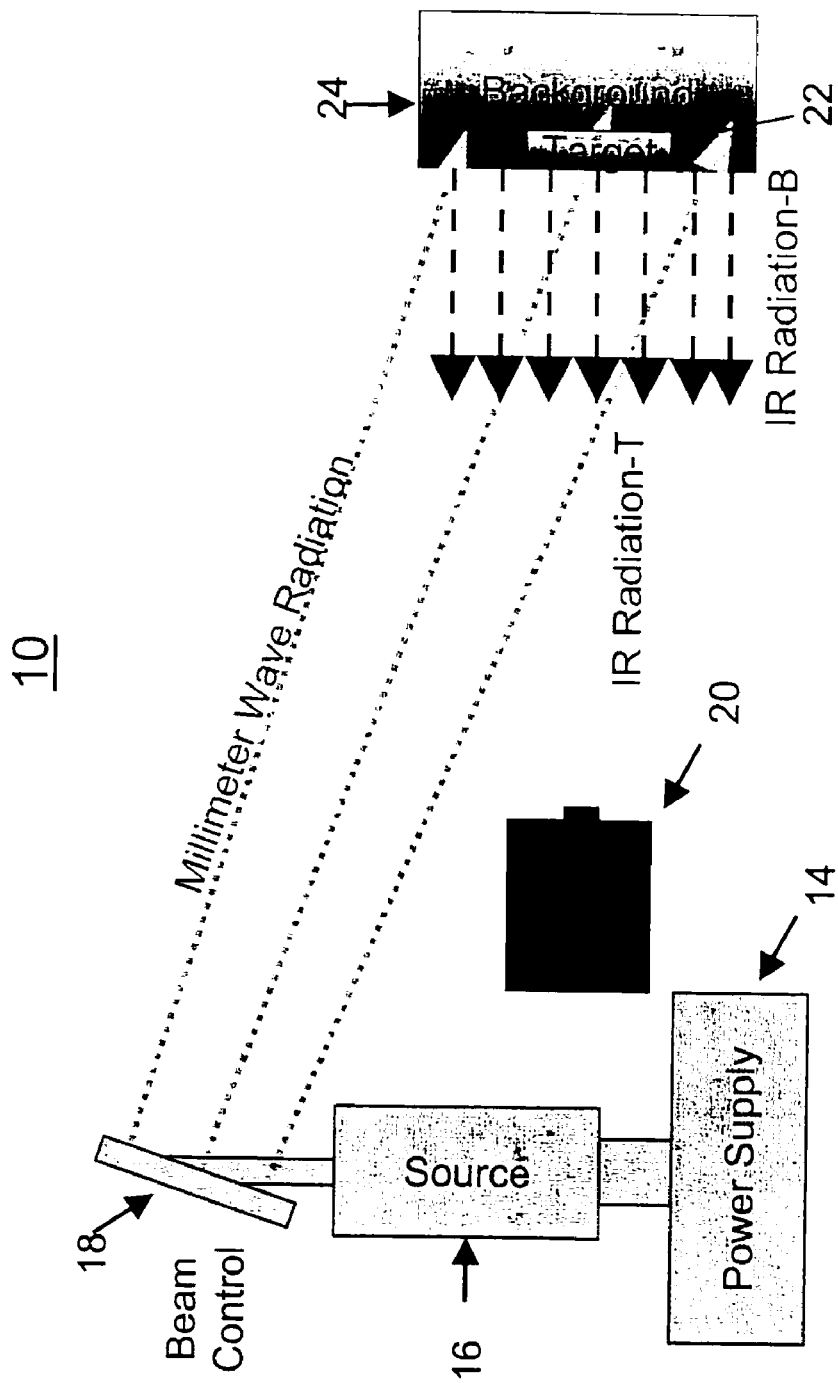
FIG. 1 is a system for active thermal imaging using a millimeter-wave source (ATIMS) according to the invention.

FIG. 1 shows a system 10 for active thermal imaging according to the invention using a millimeter-wave source (ATIMS). The system 10 includes a high voltage power supply 14, an appropriate microwave source 16, a beam controller system 18, and an infrared (IR) imaging system 20. Microwave source 16 in one embodiment is a continuous wave (CW) gyrotron for generating millimeter-length microwave radiation. The beam controller 18 preferably includes microwave components for smoothing, focusing, and directing the beam. Radiation is directed by the beam controller 18 toward a target 22, which in practice is typically surrounded by a background 24 with different material properties than the target 22. Due to the short wavelength of mm-wave radiation, the spot size of the radiation illuminating the target 22 at ranges of several hundred meters can be relatively small, thus producing sufficient intensity to heat the target and background to slightly different temperatures. This temperature difference is illustrated in FIG. 1 by the slightly different shades of IR radiation emitted from the surface of the target and background. The emitted IR radiation is captured by the IR imaging system 20.

The system 10 thus produces a high frequency microwave or millimeter-wave heating beam that can be projected over relatively long distances, e.g. on the order of 100 m or greater. This can also be applied to image buried or hidden features or objects, in addition to imaging objects that are in plain sight or are only partially obscured. The heating and detection is much more rapid than with conventional prior art microwave sources because millimeter waves interact much more strongly with most materials than do conventional S-band microwaves. The characteristic absorption lengths are particularly short in biological materials. Because infrared emissions would be attenuated with depth, deep penetration of the heating source is often not particularly desirable.

A simple theoretical model that can be used to estimate the heating of a target material by the invention is as follows. For uniform illumination of a simple target, the temperature rise in the target can be described by a one dimension heat flow equation with a source term, as is described in M. N. Öziik, *Heat Conduction*, John Wiley & Sons, New York, 1993 and P. J. Riu, K. R. Foster, D. W. Blick, and E. R. Adair, "A Thermal Model for Human Thresholds of Microwave-Evoked Warmth Sensations," *Bioelectromagnetics* 18, 578 (1996). Other processes, such as radiative losses and convection, are generally small in the regime of interest. The temperature T is then described by $$\rho c_p \frac{\partial T}{\partial t} = k_h \nabla^2 T + Q(x, t), \tag{1}$$

where $\rho$, $c_p$, and $k_h$ are the mass density, specific heat, and thermal conductivity of the target material, and Q is the power per unit volume deposited in the body. If x denotes the distance from the surface of the target, then $$Q(x, t) = \frac{I_o(t) \Lambda}{\delta} \exp(-x/\delta). \tag{2}$$

Here $I_0$ is the source intensity, $\Lambda$ is the power transmission coefficient, and $\delta$ is the depth at which the intensity falls by 1/e. Both $\Lambda$ and $\delta$ are functions of the dielectric constants in the propagation region ($\in_1$) and target material ($\in_2$). $I_0$ is the source intensity, is the power transmission coefficient, and B is the depth at which the intensity falls by 1/e. Defining the normalized real and imaginary dielectric constants $\in'=\text{Re}(\in_2)/\in_1$, and $\in''=\text{Im}(\in_2)/\in_1$, the transmission coefficient is given by $$\Lambda = \left(\frac{2}{\sqrt{\varepsilon'} + 1}\right)^2, \tag{3}$$

and the skin depth $\delta$ is given by $$\delta = \frac{1}{2k_0\sqrt{\varepsilon''}}, \tag{4}$$

where $k_0$ is the wavenumber of the incident source in the propagation region.

The heat flow equation can be solved analytically if the intensity and material properties do not change with time. It is instructive to consider the simpler case where thermal conduction is neglected. This is valid for times short compared with the characteristic thermal diffusion time, which varies typically from a fraction of a second to a few minutes for materials of interest. The change in the surface temperature rises linearly with t with a heating rate given by $$dT_0/dt = Q/\rho c_p = (\Lambda/\rho c_p \delta)I_0 \equiv \alpha^* I_0. \tag{5}$$

The heating rate constant $\alpha^* = \Lambda/\rho c_p \delta$ is a function of the source wavelength and target material properties. If two materials with heating rate constants $\alpha_1^*$ and $\alpha_2^*$ are illuminated by the same source, the temperature difference or thermal contrast between them is given by $$T_{02} - T_{01} = (\alpha_2^* - \alpha_1^*) I_0 t. \tag{6}$$

The intensity and illumination time must be sufficiently large so that the thermal contrast can be readily detected. Note that differences in emissivity may make it possible to distinguish details or targets even when the temperature difference is small.

The thermal diffusion time scales inversely with the thermal conductivity $k_h$ and is given by $$\tau_h = \frac{\delta^2 \rho c_p}{k_h}. \tag{7}$$

If thermal diffusion is included, Eq. (1) can be solved analytically for the temperature rise $\Delta T$. Defining $T^* = \delta \Lambda I_0/k_h$, and $\alpha = k_h/\rho c_p$, the temperature rise is given by $$\Delta T = \frac{T^*}{2}\left[\exp\left(\frac{t}{\tau_h} - \frac{x}{\delta}\right)\text{Erfc}\left(\sqrt{\frac{\tau_h}{t}}\left(\frac{t}{\tau_h} - \frac{x}{2\delta}\right)\right) + \right. \tag{8}$$

$$\exp\left(\frac{t}{\tau_h} + \frac{x}{\delta}\right)\text{Erfc}\left(\sqrt{\frac{\tau_h}{t}}\left(\frac{t}{\tau_h} + \frac{x}{2\delta}\right)\right)\right] +$$

$$T^*\left[\frac{2}{\sqrt{\pi}}\exp\left(\frac{-x^2}{4\alpha t}\right)\sqrt{\frac{t}{\tau_h}} - \frac{x}{\delta}\text{Erfc}\left(\frac{x}{\sqrt{4\alpha t}}\right) - \exp\left(\frac{-x}{\delta}\right)\right].$$

Here Erfc is the complementary error function.

The emitted infrared signature is determined by the surface temperature at x=0. In this case, Eq. (8) becomes $$\Delta T(0, t) = T^*\left[\exp\left(\frac{t}{\tau_h}\right)\text{Erfc}\left(\sqrt{\frac{t}{\tau_h}}\right) + \sqrt{\frac{4t}{\pi\tau_h}} - 1\right]. \tag{9}$$

In this manner, the temperature rise as a function of time can be estimated for any material whose density, heat capacity, dielectric constant, and thermal conductivity can be specified or estimated. For times that are short compared with the thermal conduction time $\tau_h$, the surface temperature rise can be estimated simply from (5). Eq. (9) can be used for $\Delta T(0, t)$ when thermal conduction is important, and the more general solution (8) can be used if a knowledge of the subsurface temperature is desired.

Table 1 gives representative values for the material properties $\in'$, $\in''$, $\rho C_p$, and $k_h$, and the derived quantities, $\Lambda$, $\delta$, $\tau_h$, and $\alpha^*$ for various target materials of interest and a 94 GHz source frequency. The materials are arranged in order of the nominal heat rate coefficient $\alpha^*$. The materials with the fastest heating rates are generally biological materials. As expected, these materials tend to have short absorption lengths and thermal conduction times. The temperature increase would rise quickly but level off due to thermal conduction. The materials with intermediate heating rate coefficients tend to have significant water content and would probably produce a small but measurable thermal signature. The materials with the smallest heating rate coefficients have very long thermal conduction times and would produce weak thermal signatures that increase linearly with time.

left. For rubber, the target heats by 0.08° C. in two seconds, and the radiation penetrates relatively deeply into the target ($\delta=0.64$ cm). For skin, the temperature reaches 0.3° C. in two seconds, but the penetration depth of the radiation is much shorter ($\delta=\mathbf{0.02}$ cm), so the interior is not heated significantly. This short penetration depth results in a short thermal conduction time (0.6 s) and a significant slowing of the heating rate at the surface at longer times.

A CW gyrotron is preferable for the invention, particularly for applications in the 94 GHz range with the pulsing of the source (to provide temporal heating/cooling rates) provided

TABLE 1

Representative values for the material properties $\epsilon'$, $\epsilon''$, $\rho C_p$, and $k_h$, and the derived quantities, $\Lambda$, $\delta$, $\tau_h$, and $\alpha^*$ for various target materials of interest.

| Material | $\epsilon'$ | $\epsilon''$ | $\rho C_p$ (J/cm$^3$-K) | $k_h$ (W/cm-K) | $\Lambda$ | $\delta$ (cm) | $\tau_h$ (sec) | $\alpha^*$ (cm$^2$K/J) |
|---|---|---|---|---|---|---|---|---|
| Dry Wood | 6 | 1.1 | 0.187 | 0.004 | 0.34 | 0.11 | 0.60 | 15.83 |
| Leather (20%H20) | 3.9 | 0.85 | 0.8 | 0.0014 | 0.45 | 0.12 | 8.05 | 4.76 |
| Skin | 5.686 | 6.603 | 4.2 | 0.003 | 0.35 | 0.02 | 0.60 | 4.03 |
| Rubber | 3.6 | 0.15 | 1.77 | 0.002 | 0.48 | 0.64 | 365.49 | 0.42 |
| Moist Sand | 4.4 | 0.2 | 2.64 | 0.027 | 0.42 | 0.53 | 27.76 | 0.30 |
| Water | 76.7 | 12 | 4.29 | 0.0222 | 0.04 | 0.04 | 0.27 | 0.26 |
| Nylon | 3.16 | 0.036 | 1.94 | 0.0025 | 0.52 | 2.51 | 4880 | 0.11 |
| Dry sand | 2.55 | 0.0158 | 1.27 | 0.0035 | 0.59 | 5.13 | 9560 | 0.09 |
| Plexiglas | 2.6 | 0.0148 | 1.64 | 0.002 | 0.59 | 5.53 | 25,110 | 0.06 |
| Phenolic | 2.8 | 0.007 | 1.5 | 0.0018 | 0.56 | 12.14 | 123,000 | 0.03 |
| Ice | 3.2 | 0.0029 | 2.2 | 0.0222 | 0.51 | 31.55 | 98,600 | 0.01 |

Figure 2:
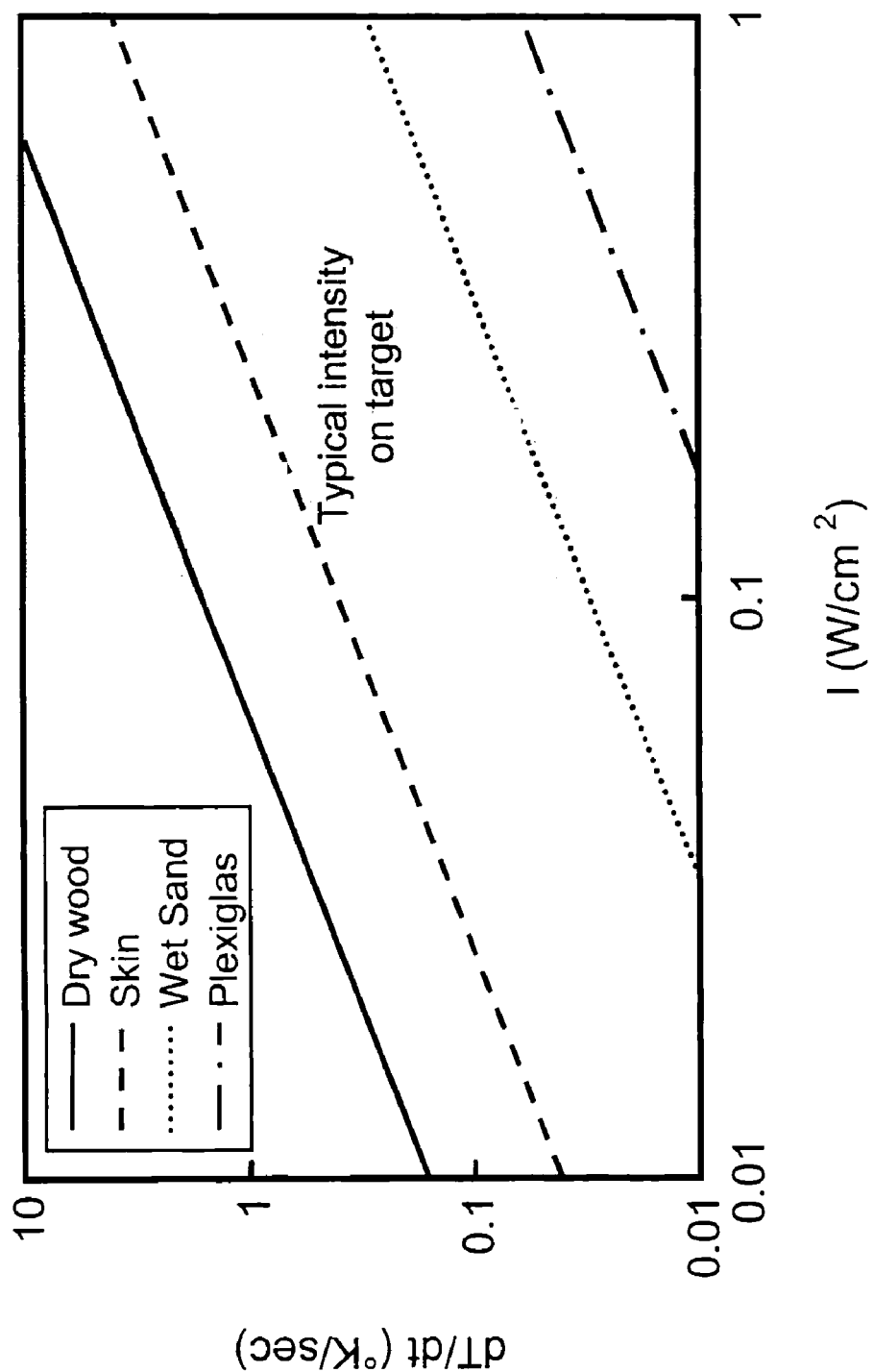
FIG. 2 is a graph showing the nominal heating rate $dT_0/dt$ at a target surface as a function of the heating radiation intensity $I_0$ for four different materials according to the invention.

FIG. 2 plots the nominal heating rate $dT_s/dt$ at the surface using Eq. (5) as a function of the heating radiation intensity $I_0$ for four different materials, using the data in Table 1. This nominal rate neglects thermal conduction. The selected materials illustrate a broad range of heating rates. The difference in any two lines gives the thermal contrast for those two materials after 1 second of heating at a given intensity. Dry wood and skin heat quickly, while wet sand exhibits a modest heating rate, and Plexiglas heats very little. Preferably system 10 is operated at an intensity that heats a weakly-heated material such as wet sand by approximately 0.1° K/s. In the absence of thermal conduction, this requires an intensity greater than $0.1/\alpha^*$[W/cm$^2$]. Areas or targets that heat more slowly will still stand out provided that there are nearby objects or background areas that do heat up. Intensities on target of 0.1-0.5 W/cm$^2$ are preferable in order to satisfy these criteria. This range of intensities is shown as the shaded area in FIG. 2.

Figure 3:
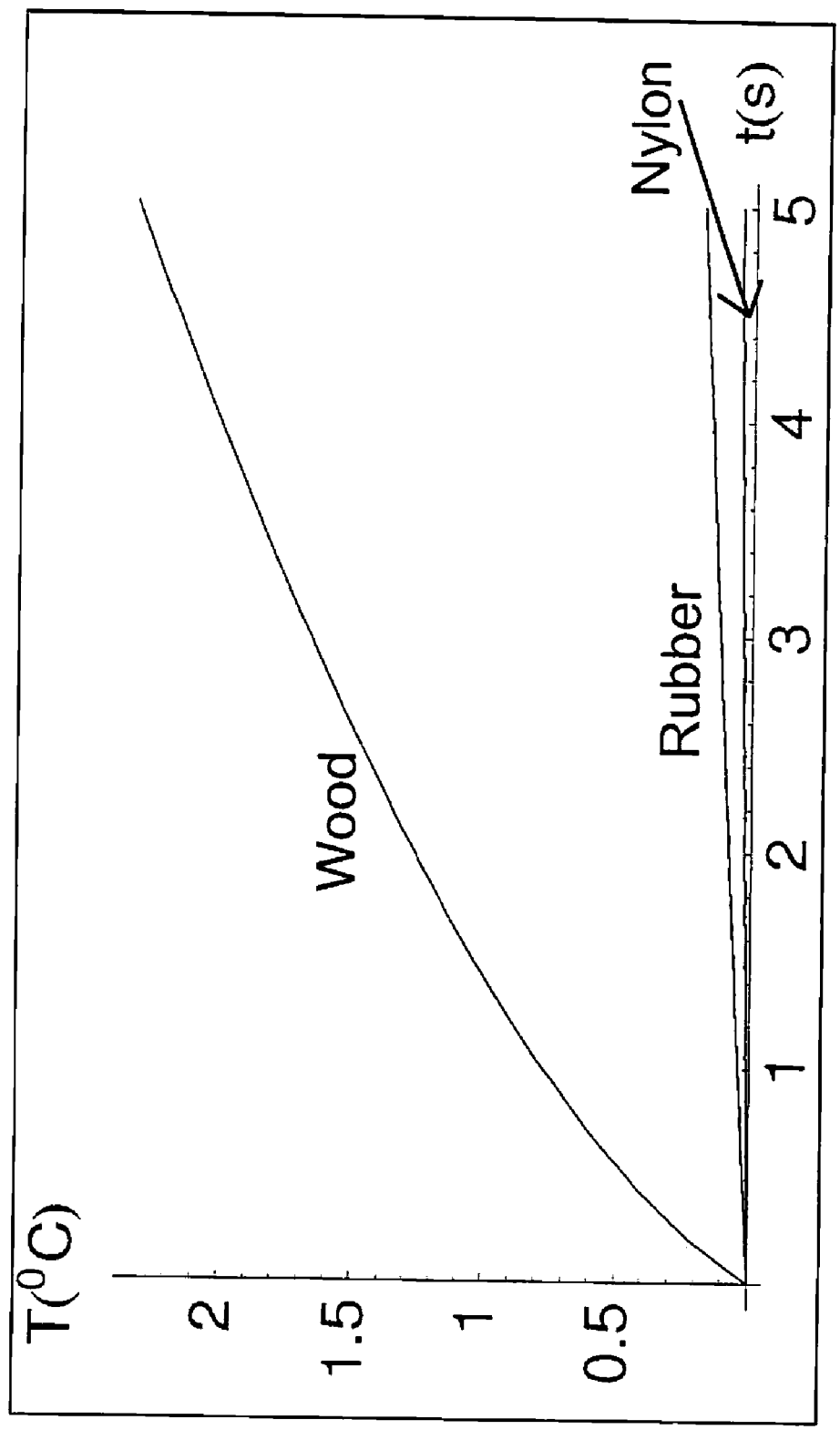
FIG. 3 is a graph showing the surface temperature rise $\Delta T(0,t)$ for three different materials using a 94 GHz source at an intensity of 0.1 W/$cm^2$ according to the invention.

The actual surface temperature as a function of time can be calculated for a given material and source intensity using Eq. (9). FIG. 3 plots the surface temperature rise $\Delta T(0,t)$ for three different materials using a 94 GHz source at an intensity of 0.1 W/cm$^2$. Even at this relatively modest intensity, measurable thermal contrast between wood and the other two materials can be produced after 1-2 seconds of heating. Since the thermal conduction time for wood is only 0.60 s, the plot exhibits the expected slowing of the heating rate heating rate at later times. Although the thermal contrast between rubber and nylon is much weaker, increasing the intensity by a factor of 3-5 would raise the contrast to a level that could probably be easily detected.

Figure 4B:
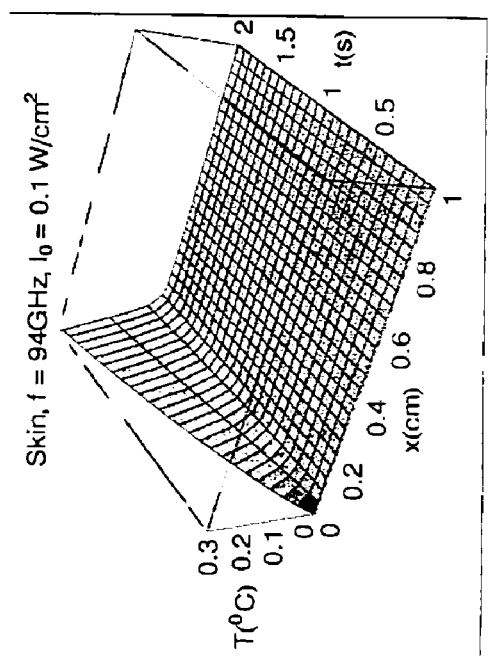
FIGS. 4A and B are 3-D spatial-temporal graphs illustrating the temperature increase $\Delta T(x,t)$ for rubber (FIG. 4A) and skin (FIG. 4B) heated by a 94 GHz source at 0.1 W/$cm^2$ according to the invention.
Figure 4A:
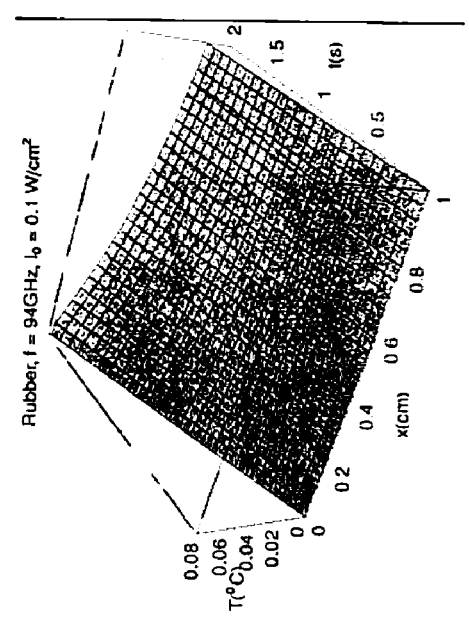

The solution to the 1-D heat equation given in Eq. (8) is plotted in FIG. 4 as functions of time t and distance x into the target material. FIG. 4A is for rubber, which has a moderate heating rate, while FIG. 4B is for skin, which heats more quickly. The millimeter wave source parameters are the same as in FIG. 3. The radiation propagates into the target from the by sweeping of the beam. The source should be robust and capable of providing reasonably uniform illumination of the target area at ranges of interest. Long-range applications will generally require the source to be transportable. The source should provide sufficient intensity to raise the surface temperature by a detectable amount. Conventional S-band microwave sources operating at 2.45 GHz are not ideal because the radiation cannot be focused with a reasonable antenna size, and this frequency does not couple well to most materials. High frequency (millimeter wave) sources using CW gyrotrons generate radiation that can be focused with a much smaller antenna and couple much more strongly to most materials. High intensity millimeter wave sources, e.g. as described in W. Fliflet, R. W Bruce, R. P Fischer, D. Lewis, III; L. K Kurihara, B. A Bender, G.-M Chow, and R. J Rayne, "A Study of Millimeter-Wave Sintering of Fine-Grained Alumina Compacts," IEEE Trans. Plasma Sci. 28, 924 (2000) and D. Lewis, M. A. Imam, L. K. Kurihara, A. W. Fliflet, A. Kinkead, S. Miserendino, S. Egorov, R. W. Bruce, S. Gold, A. M. Jung, "Material processing with a high frequency millimeter-wave source," Materials and Manufacturing Processes, 18, 151 (2003), have been used for a variety of materials processing applications that require rapid heating by hundreds of degrees.

At more moderate intensities, gyrotron sources capable of raising skin temperatures by tens of degrees in seconds are being studied for active denial applications, e.g. as described in Naval Studies Board, *An Assessment of Non-Lethal Weapons Science and Technology* (2003), National Academies Press, Washington, D.C., 2003. At still lower intensities, a focused millimeters-wave source should be capable of raising the temperature in a thin layer in the target by approximately 1 degree Centigrade. Because IR cameras can be sensitive to differences in temperature of a few hundredths of a degree Centigrade, 1 degree is certainly sufficient to be observable.

Other sources include the gyro-klystron, which is used in a Navy high power radar test facility at the Naval Research Laboratory's Chesapeake Bay Detachment, and which provides substantial average power with the possibility of operating as a radar. However, this device is substantially larger and more complex than a CW gyrotron. The choice of frequency depends in part on the desired application. Higher frequencies generally offer less penetration depth, which reduces the required energy on target. However, the scaling of power with frequency for a given class of sources is not favorable, and for frequencies above 100 GHz, the lower intensity advantage is generally counterbalanced by reduced source power and increased source cost and complexity. Among higher frequency choices, 140 GHz is desirable because there is a local minimum in the atmospheric absorption coefficient at that frequency.

Among lower frequency sources, 35 GHz propagates well in the atmosphere and is a desirable choice. In general, the penetration depth is longer, which can be desirable for applications requiring subsurface heating but requires more energy to be deposited on target. Lower frequency sources are generally simpler and cheaper but may require a larger antenna. For applications at shorter ranges or longer heating times, such as nondestructive evaluation, a less powerful source may be appropriate. In these cases, cost and portability may be considerations, and a smaller, less expensive imaging system may be appropriate. Examples of this would be finding electronic devices planted in drywall or devices planted under clothing.

Figure 5:
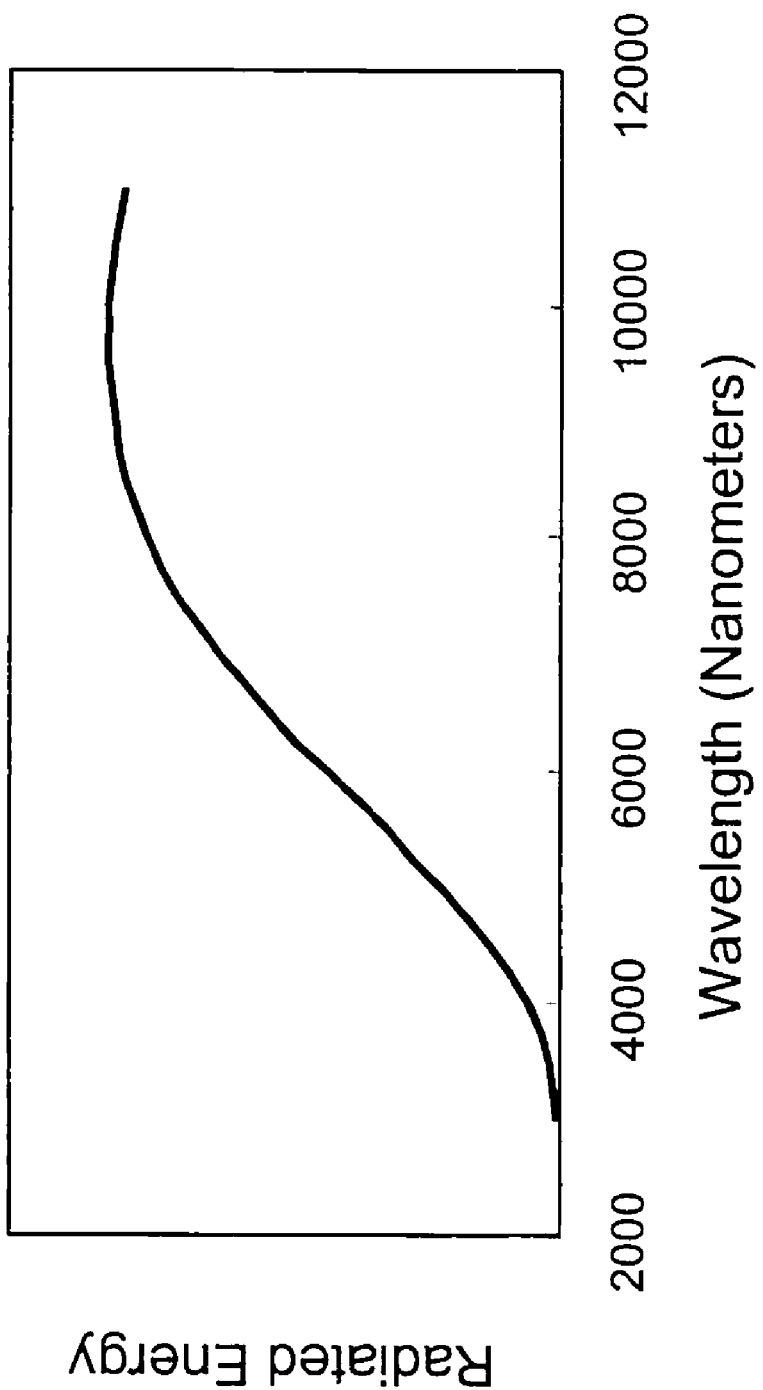
FIG. 5 is a graph showing a spectrum of radiated energy versus wavelength for a blackbody emitter at 300° K.

IR imaging system 20 in one embodiment employs passive IR detection, which is widely used and is capable of detecting extremely small temperature differences in targets. Unless otherwise stated the assumption here is that the materials emit as blackbodies and not with significant spectral shape. Large temperature contrasts can be readily seen employing inexpensive video cameras operating in the near infrared, but these are best suited for objects at high temperatures. For objects at room temperature (300 K), the peak of the blackbody radiation spectrum occurs at ~10 µm wavelength (FIG. 5), which lies in the long wavelength range (LWIR) atmospheric transmission window.

Any material above absolute zero radiates energy. The amount and spectral shape of the emitted radiation depends on the temperature and the emissivity of the material. The temperature controls the spectral shape as detailed by Planck's Radiation Law. A true blackbody (with emissivity of 1) will emit the full amount of radiation described by Planck's Law. Most materials have an emissivity that is less than 1 and they emit that fraction of the radiation laid out by Planck's Law. Thus two variables, temperature and emissivity, describe the emitted radiation spectral shape and magnitude. The noise characteristics of the imaging system therefore need to be considered when choosing which transmission band is most applicable to a particular problem.

Figure 6:
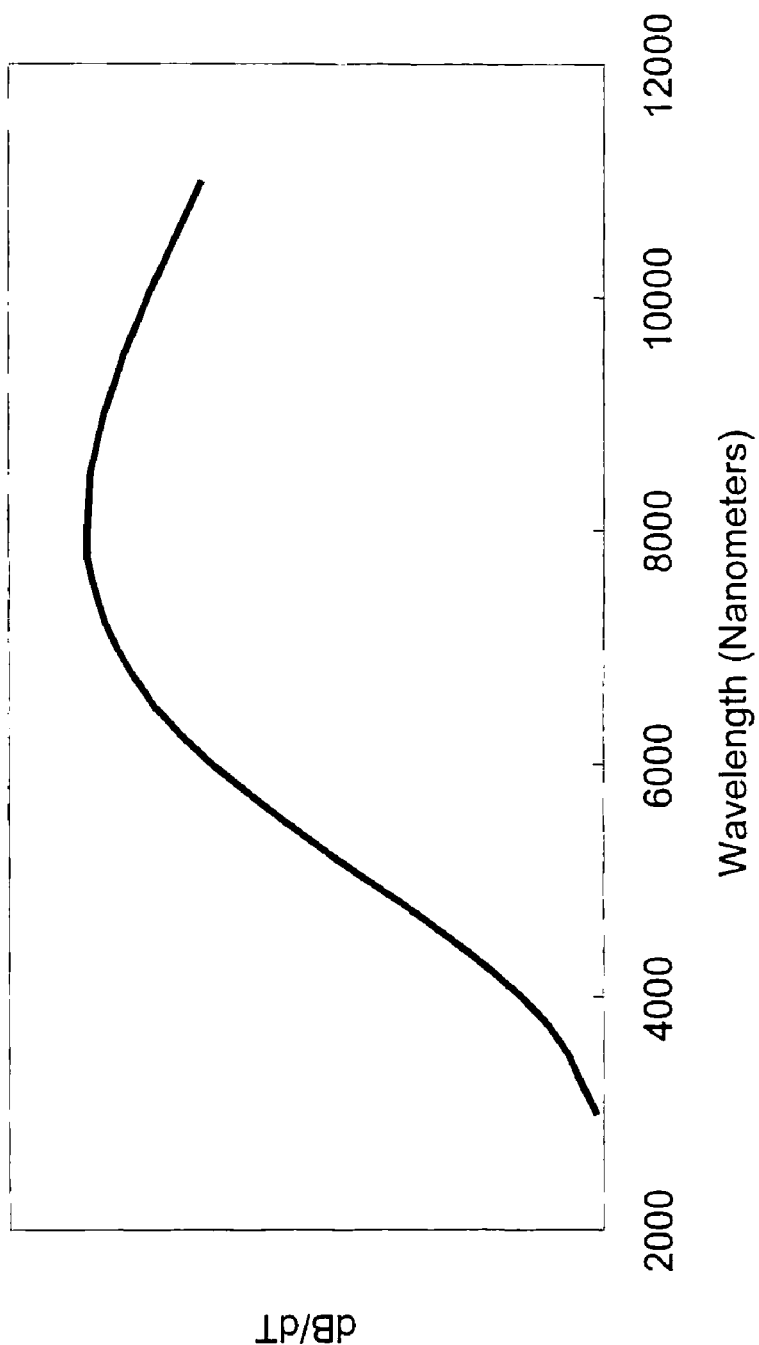
FIG. 6 is a graph showing a spectrum of the differential emission dB/dT versus wavelength for a blackbody emitter at 300° K.

As previously stated the peak in the radiated energy is near 10 microns for a room temperature material. However, the fundamental measurement to be made is the change in emission as materials are heated. As shown in FIG. 6, the peak in the change in emission with temperature is closer to 8 microns for room temperature. This means that as the temperature of the material increases that the energy radiated at 8 microns will increase the fastest and thus may be the best wavelength to image. However, as a fraction of the emitted energy, the changes in the 3 to 5 micron area are about a factor of 2 times higher than in the LWIR region. This 3 to 5 micron wavelength regime corresponds to the mid wavelength infrared (MWIR) transmission window where the characteristic absorption length in the atmosphere is several kilometers.

In one embodiment, IR imaging system 20 utilizes a MWIR broadband camera (e.g. having a sensitivity in the range of from about 3 to about 5 microns) to measure the emitted energy integrated over the wavelength range and capable of generating a two-dimensional temperature map of the target area. Sensors currently available for this wavelength range offer the highest signal to noise and provide the best opportunity to detect very small changes in emitted energy. In a related embodiment, the IR imaging system 20 utilizes a LWIR broadband camera (e.g. having a sensitivity in the range of from about 8 to about 12 microns). This wavelength also corresponds to an atmospheric transmission window.

The system 10 may further include a hyperspectral imaging spectrometer for processing the IR image data received from the target 22, such as is described in "Hyperspectral visualization extensible workbench," U.S. Pat. No. 6,771,798, D. G. Haas, et al. issued Aug. 3, 2004, incorporated herein by reference. In these systems, the signal is passed through a spectrometer so image intensity is recorded as a function of one spatial dimension and wavelength or frequency. By sweeping the recording strip, a 3-D hypercube representing wavelength and two spatial dimensions may be generated. Hyperspectral imaging combined with an active thermal imaging source 20 accordingly produces additional useful information (measuring emissivity and temperature and measuring scattered radiation and outgassing chemical vapors) for identifying targets.

Experiments that demonstrate the operation of the invention have been performed in a controlled laboratory setting. Referring to the generic system 10 shown in FIG. 1, the millimeter wave source 16 was an 83 GHz, 20 kW CW gyrotron with an appropriate high voltage power supply 14. The source was located in a facility designed primarily for heating ceramics to high temperatures for materials processing applications such as bonding and sintering. The beam director 18 was a simple metal reflector that produced a heating beam with an intensity of approximately 0.5 W/cm$^2$ at the bottom of an enclosed target chamber. Because the heated area was only 100 cm$^2$, the source was operated in a very low power mode. The infrared imaging system 20 was a cryogenically-cooled Merlin Mid IR camera (Indigo Systems) with a nominal temperature sensitivity of 0.015° C. When the millimeter-wave heating source was turned on, this camera acquired infrared images of the target at up to 60 frames per second. Each frame of the camera data was processed to produce a two-dimensional image of the temperature distribution in the target area. Although these experiments were conducted at low powers and short ranges, the thermal response of the target is determined by the intensity of the beam onto the target, not the total beam power. Thus, if the 20 kW system operated at full power with an appropriate beam director, it could produce the same thermal signature at much longer ranges and over a much larger area.

Figure 7B:
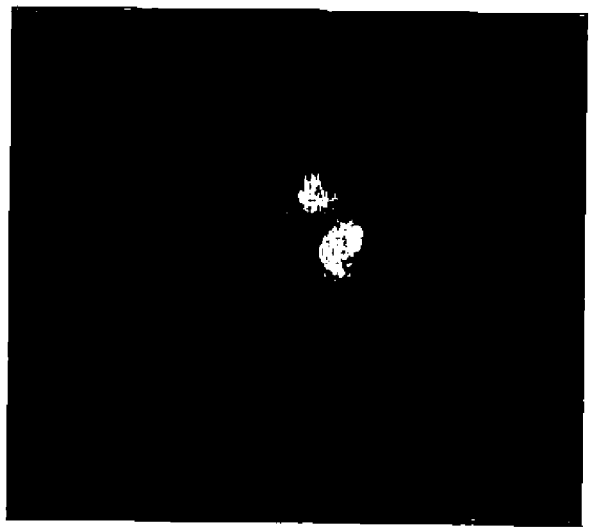
FIG. 7B shows a thermal image of two of the objects (metal, wood) heated by a ~100 $cm^2$ beam with 2 seconds of heating. The third object (Teflon) remained at essentially the same temperature as the background.
Figure 7A:
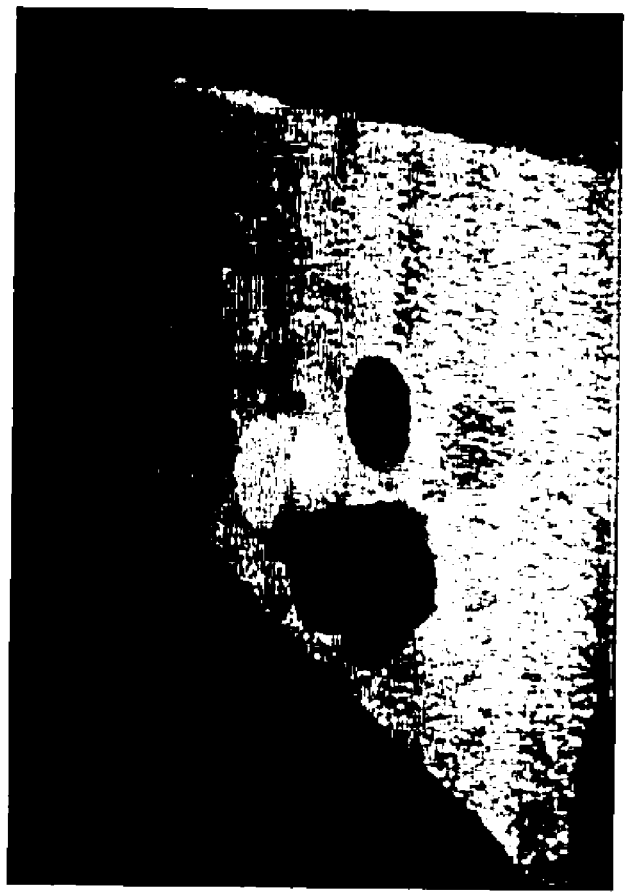
FIG. 7A shows the target setup for an experiment in which three objects (wood, metal, and Teflon) were placed on a weakly-absorbing background (brick) and covered with a cotton cloth.

Data was taken for a variety of small targets and configurations, including many in which the target was obscured by cloth or sand. As expected, heating rates for simple targets varied widely, depending on the material being heated. The thermal image of objects hidden by cloth was readily apparent in a variety of situations. Metal objects remained cool when illuminated directly but often produced a strong thermal signature when one or more layers of cloth were placed over them. FIG. 7A shows the target setup for an experiment in which three objects (wood, metal, and Teflon) were placed on a weakly-absorbing background (brick) and covered with a cotton cloth. FIG. 7B shows a thermal image of two of the objects (metal, wood) heated by a ~100 cm² beam with 2 seconds of heating. The third object (Teflon) remained at approximately the same temperature as the brick background and is not readily apparent.

Figure 8B:
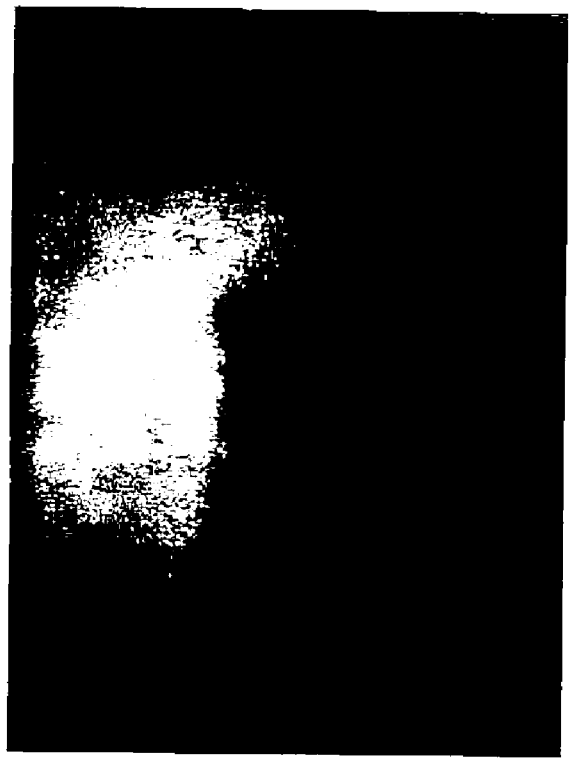
FIG. 8B shows the thermal image of the same object and background shown in FIG. 8A when both are covered by a cloth. The image was taken during the cooling period after the millimeter-wave beam had been turned off.
Figure 8A:
FIG. 8A shows the thermal image of a rectangular metal object (dark) against a strongly-absorbing background (bright) in an area heated by a millimeter-wave beam.

In FIG. 8A, a rectangular metal object was placed on a strongly-absorbing background (wood) was heated by a broader (~10³ cm²) beam. The metal (dark area) stayed cool relative to the strongly-heated background, and the thermal contrast is quite distinct. The lighter area shows the direct heating of the wood by the millimeter-wave beam. In FIG. 8B, a cloth cover was placed over the metal object and wood background. The image shown was taken several seconds after the heating beam was turned off. For this case where the object was hidden, the thermal contrast was significantly stronger during this cool down period than it was during the time that the heating radiation was applied. Thus, it may also be desirable in some cases to pulse the heating source and to continue to monitor the target area as it cools.

For some long range imaging applications, it is desirable to introduce a thermal contrast between a target 22 and the background or clutter. If the target does not generate its own internal heating or cooling source and has not moved recently, its temperature will be very near that of the background. When irradiated by the ATIMS source 12, the target and background will heat at different rates. If the target and background are initially at the same temperature, it will not matter whether the target heats faster or slower than the background provided a measurable thermal contrast can be produced.

An active thermal imaging signature may be produced in several different target-background scenarios. For an unobscured target 22 in a cluttered background 24, the induced temperature change may cause the target to stand out more distinctly against the background as the thermal contrast increases. This could be particularly important when the target has been painted to blend in with the background. For example, an unobscured but camouflage-painted metal object will probably heat more slowly than the background. For a partially-obscured target, portions of the target may again heat at a different rate than the obscuring object, thus producing a detectable thermal contrast. The vegetation will probably heat more rapidly, and the thermal signature of the localized cool spots from the target will be enhanced. A final example is a fully concealed target that is in thermal contact with a thin, obscuring object. A particularly important example of this case is a bomb concealed under clothing. If the radiation from the heating source penetrates to the concealed target and heats it at a different rate, a thermal signature from the surface of the obscuring object may be detectable.

For short range imaging applications, an ATIMS source 12 may also be suitable for nondestructive evaluation (NDE) and other short range or laboratory applications. Again, the goal would be to introduce thermal contrasts in a target or object that might reveal useful information. Several groups have used conventional S-band microwave sources as an IR thermography technique for imaging subsurface properties. Targets have included layered dielectrics, concrete structures, and subsurface land mines, as described above.

An ATIMS NDE system with a millimeter wave source has some of the same advantages discussed above for long range applications. The absorption length is generally much shorter, so the mass of material heated is less, and the heating is much more rapid. The radiation can be focused into a beam, so that there can be a substantial standoff distance between the source and the target. This could be useful for imaging defects in building structures, for example. In general, the standoff distance and speed requirements for NDE applications will be less stressing than for military standoff detection applications. This would permit the use of a smaller, less expensive heating source.

Obviously many modifications and variations of the present invention are possible in the light of the above teachings. It is therefore to be understood that the scope of the invention should be determined by referring to the following appended claims.

What is claimed as new and desired to be protected by Letters Patent of the United States is:

1. A method of obtaining a thermal image of a target, comprising:
   directing an electromagnetic radiation from a microwave source directly onto the target to produce an infrared response in and infrared radiation emission directly from the target;
   receiving the infrared radiation emission in an infrared imager; and
   generating a series of thermal images of the target wherein a measured initial temperature variation within the target area is removed by an averaging process in the thermal imaging data.

2. The method of claim 1, wherein the target includes completely exposed objects or surface details whose heating rate is different from the surrounding background or clutter, resulting in those objects or surface details to stand out in the series of thermal images.

3. The method of claim 1, wherein the target includes a subsurface element in thermal contact with a thin, obscuring object.

4. The method of claim 3, wherein the obscuring object is clothing and the subsurface element is a weapon or explosive device.

5. The method of claim 1, wherein the target includes a partially obscured object whose induced temperature change in its exposed portions causes it to stand out more clearly from the obscuring object or background in the series of thermal images.

6. The method of claim 1, wherein the nominal heating rate coefficient and thermal conduction time associated with the material composition of an exposed object or surface feature may be deduced from the series of thermal images.

7. The method of claim 6, wherein the possible material composition of an exposed object or material may be deduced from the nominal heating rate and thermal conduction time.

8. A method of obtaining a thermal image of a target, comprising:
   directing an electromagnetic radiation from a microwave source directly onto a target to produce an infrared response in and infrared radiation emission directly from the target;
   receiving the infrared radiation emission in an infrared imager; and
   generating a series of thermal images of the target, wherein an energy density of the electromagnetic radiation at the target is raised in order to produce a nonthermal signature of the target.

9. A method of obtaining a thermal image of a target, comprising:
   directing an electromagnetic radiation from a microwave source directly onto a remote target to produce an infrared response in and infrared radiation emission directly from the target;
   receiving the infrared radiation emission in an infrared imager; and generating a series of thermal images of the target where an enhanced chemical vapor outgassing is detected via optical emission or absorption.

10. A method of obtaining a thermal image of a target, comprising:
- directing an electromagnetic radiation from an electromagnetic radiation source for emitting radiation in a frequency range of from about 10 GHz to about 500 GHz, directly onto a remote target to produce an infrared response in and infrared radiation emission directly from the target;
- receiving the infrared radiation emission in an infrared imager; and
- generating a series of thermal images of the target wherein a measured initial temperature variation within the target area is removed by an averaging process in the thermal imaging data.

11. The method of claim 10, wherein the target includes completely exposed objects or surface details whose heating rate is different from the surrounding background or clutter, resulting in those objects or surface details to stand out in the series of thermal images.

12. The method of claim 10, wherein the target includes a subsurface element in thermal contact with a thin, obscuring object.

13. The method of claim 12, wherein the obscuring object is clothing and the subsurface element is a weapon or explosive device.

14. The method of claim 10, wherein the target includes a partially obscured object whose induced temperature change in its exposed portions causes it to stand out more clearly from the obscuring object or background in the series of thermal images.

15. The method of claim 10, wherein the nominal heating rate coefficient and thermal conduction time associated with the material composition of an exposed object or surface feature may be deduced from the series of thermal images.

16. The method of claim 15, wherein the possible material composition of an exposed object or material may be deduced from the nominal heating rate and thermal conduction time.

17. The method of claim 10, wherein the frequency range is from about 35 GHz to about 140 GHz and the target is at a distance of at least 100 meters from the electromagnetic radiation source.

18. A method of obtaining a thermal image of a target, comprising:
- directing an electromagnetic radiation from an electromagnetic radiation source for emitting radiation in a frequency range of from about 10 GHz to about 500 GHz, directly onto a remote target to produce an infrared response in and infrared radiation emission directly from the target;
- receiving the infrared radiation emission in an infrared imager; and
- generating a series of thermal images of the target wherein an energy density of the electromagnetic radiation at the target is raised in order to produce a nonthermal signature of the target.

19. The method of claim 18, wherein the frequency range is from about 35 GHz to about 140 GHz and the target is at a distance of at least 100 meters from the electromagnetic radiation source.

20. A method of obtaining a thermal image of a target, comprising:
- directing an electromagnetic radiation from an electromagnetic radiation source for emitting radiation in a frequency range of from about 10 GHz to about 500 GHz, directly onto a remote target to produce an infrared response in and infrared radiation emission directly from the target;
- receiving the infrared radiation emission in an infrared imager; and
- generating a series of thermal images of the target where an enhanced chemical vapor outgassing is detected via optical emission or absorption.

21. The method of claim 20, wherein the frequency range is from about 35 GHz to about 140 GHz and the target is at a distance of at least 100 meters from the electromagnetic radiation source.

* * * * *